United States Patent
Riesmeyer et al.

(10) Patent No.: US 11,890,325 B2
(45) Date of Patent: Feb. 6, 2024

(54) THERAPEUTIC USES OF DULAGLUTIDE

(71) Applicant: Eli Lilly and Company, Indianapolis, IN (US)

(72) Inventors: Jeffrey S. Riesmeyer, Indianapolis, IN (US); David Bradley Woodward, Fishers, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 6 days.

Patent file contains an affidavit/declaration under 37 CFR 1.130(b).

(21) Appl. No.: 17/599,621

(22) PCT Filed: Nov. 4, 2019

(86) PCT No.: PCT/US2019/059631
§ 371 (c)(1),
(2) Date: Sep. 29, 2021

(87) PCT Pub. No.: WO2020/204998
PCT Pub. Date: Oct. 8, 2020

(65) Prior Publication Data
US 2022/0202908 A1    Jun. 30, 2022

Related U.S. Application Data

(60) Provisional application No. 62/829,717, filed on Apr. 5, 2019.

(51) Int. Cl.
*A61K 38/26* (2006.01)
*A61P 3/10* (2006.01)
*A61K 31/616* (2006.01)
*A61K 45/06* (2006.01)

(52) U.S. Cl.
CPC ............ *A61K 38/26* (2013.01); *A61K 31/616* (2013.01); *A61K 45/06* (2013.01); *A61P 3/10* (2018.01)

(58) Field of Classification Search
CPC .......... A61K 38/26; A61K 31/616; A61P 3/10
See application file for complete search history.

(56) References Cited

U.S. PATENT DOCUMENTS

| | | | |
|---|---|---|---|
| 7,084,243 B2 | 8/2006 | Glaesner et al. | |
| 7,271,149 B2 | 9/2007 | Glaesner et al. | |
| 7,452,966 B2 | 11/2008 | Glaesner et al. | |
| 9,949,997 B2 | 4/2018 | Broedl et al. | |
| 9,968,659 B2 | 5/2018 | Rasmussen | |
| 2004/0053370 A1 | 3/2004 | Glaesner et al. | |
| 2007/0036806 A1 | 2/2007 | Glaesner et al. | |
| 2009/0203603 A1 | 8/2009 | Baron et al. | |
| 2009/0232807 A1 | 9/2009 | Glaesner et al. | |
| 2010/0196405 A1 | 8/2010 | Ng | |
| 2016/0168388 A1 | 6/2016 | Barbe et al. | |
| 2020/0171129 A1 | 6/2020 | Botros et al. | |

FOREIGN PATENT DOCUMENTS

| | | | |
|---|---|---|---|
| EP | 0879279 A1 | | 8/1997 |
| EP | 3275438 | * | 1/2018 |
| WO | 2009009562 A2 | | 1/2009 |
| WO | 2011138421 A1 | | 11/2011 |
| WO | 2014187342 A1 | | 11/2014 |
| WO | 17149105 A1 | | 9/2017 |
| WO | 2017149112 A1 | | 9/2017 |

OTHER PUBLICATIONS

Davies, M., et al. "Efficacy and safety of liraglutide versus placebo as add-on to glucose-lowering therapy in patients with type 2 diabetes and moderate renal impairment (LIRA-RENAL): a randomized clinical trial." Diabetes care 39, No. 2 (2016): 222-230.

De La Peña, A., et al., "No dose adjustment is recommended for digoxin, warfarin, atorvastatin or a combination oral contraceptive when coadministered with dulaglutide" Clinical Pharmacokinetics (2017) 56(11) pp. 1415-1427.

De La Peña, A., et al., "Once-weekly dulaglutide 1.5 mg restores insulin secretion in response to intravenous glucose infusion" Diabetes, Obesity and Metabolism (2017) 19(4) pp. 517-523.

De Lucas, M., et al. "Liraglutide preserves renal function in overweight diabetic patients with stage 3 chronic kidney disease." European journal of internal medicine 44 (2017): e28-e29.

Dilla, T., et al., "The cost effectiveness of dulaglutide versus liraglutide for the treatment of type 2 diabetes mellitus in Spain in patients with BMI≥ 30 kg/m2" Journal of Medical Economics (2017) 20(5) pp. 443-452.

Divino, V., et al., "GLP-1 RA treatment patterns among type 2 diabetes patients in five European countries" Diabetes Therapy (2017) 8(1) pp. 115-128.

Dungan, K. M., et al., "Once-weekly dulaglutide versus once-daily liraglutide in metformin-treated patients with type 2 diabetes (AWARD-6): a randomised, open-label, phase 3, non-inferiority trial" The Lancet (2014) 384(9951), 1349-1357.

Dungan, K. M., et al., "A 24-week study to evaluate the efficacy and safety of once-weekly dulaglutide added on to glimepiride in type 2 diabetes (AWARD-8)" Diabetes, Obesity and Metabolism (2016) 18(50) pp. 475-482.

Dungan, K. M., et al., "Achieving the composite endpoint of glycated haemoglobin< 7.0%, no weight gain and no hypoglycaemia in the once-weekly dulaglutide AWARD programme" Diabetes, Obesity and Metabolism (2016) 18(1), pp. 49-55.

(Continued)

*Primary Examiner* — Gyan Chandra
(74) *Attorney, Agent, or Firm* — Matthew T. Lord

(57) ABSTRACT

The present invention relates to methods for reducing the risk of major adverse cardiovascular events in type 2 diabetes mellitus (T2DM) patients with multiple cardiovascular risk factors without established cardiovascular disease or with established cardiovascular disease comprising administering the glucagon like peptide-1 (GLP-1) receptor agonist dulaglutide.

8 Claims, No Drawings

Specification includes a Sequence Listing.

(56) References Cited

OTHER PUBLICATIONS

Edwards, K. L., et al., "Dulaglutide: an evidence-based review of its potential in the treatment of type 2 diabetes" Core evidence (2015) 10, 11.
Eli Lilly and Co. "Edited Transcript Q1 2019 Eli Lilly and Co Earnings Call" (2019) Thomson Reuters, Event Date Apr. 30, 2019 Time: 1:00 pm gmt.
Eli Lilly and Co. "Q2 2017 Results—Earnings Call Transcript" Seeking Alpha (Jul. 25, 2017).
Engel, S. S., et al. "Time to insulin in the Trial Evaluating Cardiovascular Outomes with Sitagliptin (TECOS)." *Diabetologia* (2017) vol. 60, pp. S3-S3. 233 Spring St, New York, NY 10013 USA: Springer.
Fahrbach, J. L., et al. Network meta-analysis accurately predicted the outcome of a subsequent randomised trial comparing once weekly dulaglutide 1.5 mg and once daily liraglutide 1.8 mg. International Journal of Clinical Practice (2016) 70(3) 218-221.
Ferdinand, K.C., et al., "Effects of the once-weekly glucagon-like peptide-1 receptor agonist dulaglutide on ambulatory blood pressure and heart rate in patients with type 2 diabetes Mellitus" Hypertension (2014) 64(4) pp. 731-737.
Ferdinand, et al. "Cardiovascular safety for once-weekly dulaglutide in type 2 diabetes: a pre-specified meta-analysis of prospectively adjudicated cardiovascular events" Cardiovascular Diabetology (2016) 15: 38.
Frias, J. P., Wynne, A. G., Matyjaszek-Matuszek, B., Bartaskova, D., Cox, D. A., Woodward, B., . . . & Milicevic, Z. (2019). Efficacy and safety of an expanded dulaglutide dose range: A phase 2, placebo-controlled trial in patients with type 2 diabetes using metformin. *Diabetes, Obesity and Metabolism*, 21(9), 2048-2057.
Gallwitz, B., et al., "Effect of once-weekly dulaglutide on HbA1c and fasting blood glucose in patient subpopulations by gender, duration of diabetes, and baseline HbA1c" Diabetes Obes Metab. (2017) Wiley, DOI: 10.1111/dom.13086.
Geiger, M. J., et al., "An adaptive, dose-finding, seamless phase 2/3 study of a long-acting glucagon-like peptide-1 analog (dulaglutide): trial design and baseline characteristics" Journal of Diabetes Science and Technology (2012) vol. 6, Issue 6, pp. 1319-1327.
Geiser, J. S., et al., "Clinical pharmacokinetics of dulaglutide in patients with type 2 diabetes: analyses of data from clinical trials" Clinical pharmacokinetics (2016) 55(5) pp. 625-634.
Gelhorn, H. L., et al., "Evaluating preferences for profiles of GLP-1 receptor agonists among injection-naive type 2 diabetes patients in the UK" Patient preference and adherence (2015) 9, 1611.
Gelhorn, H. L., et al., "Evaluating preferences for profiles of glucagon-like peptide-1 receptor agonists among injectionnaive type 2 diabetes patients in Japan" Patient preference and adherence (2016) 10, p. 1337.
Gerstein, H. C., et al. "Design and baseline characteristics of participants in the Researching cardiovascular Events with a Weekly INcretin in Diabetes (REWIND) trial on the cardiovascular effects of dulaglutide." *Diabetes, Obesity and Metabolism* 20, No. 1 (Jan. 2018): 42-49.
Gerstein H.C., et al., "REWIND Trial Investigators. Design and baseline characteristics of participants in the Researching cardiovascular Events with a Weekly INcretin in Diabetes (REWIND) trial on the cardiovascular effects of dulaglutide" Diabetes Obes Metab. (2017) doi: 10.1111/dom.13028.
Gerstein H.C., et al., "Dulaglutide and cardiovascular outcomes in type 2 diabetes (REWIND): a double-blind, randomised placebo-controlled trial" Lancet (Jul. 2019) 394:121-30.
Gerstein H.C., et al., "The effect of dulaglutide on stroke: an exploratory analysis of the REWIND Trial" Lancet Diabetes Endocrinol (Feb. 2020) 8:106-14.
Giorgino F., "Efficacy and safety of once weekly dulaglutide versus insulin glargine in patients with type 2 diabetes on metformin and glimepiride (AWARD-2)" Diabetes Care. (2015) 38(12):2241-2249.
Glaesner, W., et al. "Engineering and characterization of the long-acting glucagon-like peptide-1 analogue LY2189265, an Fc fusion protein." *Diabetes/metabolism research and reviews* 26, No. 4 (2010): 287-296.
Grunberger, G., et al., "Monotherapy with the once-weekly GLP-1 analogue dulaglutide for 12 weeks in patients with type 2 diabetes: dose-dependent effects on glycaemic control in a randomized, double-blind, placebocontrolled study" Diabetic medicine (2012) 29(10) pp. 1260-1267.
Grunberger, G., et al., "Early fasting glucose measurements can predict later glycaemic response to once weekly dulaglutide" Diabetic Medicine (2016) 33(3) pp. 391-394.
Heathman, M., et al., "The Application of Drug-Disease and Clinical Utility Models in the Design of an Adaptive Seamless Phase 2/3 STUD.: PI-87" Clinical Pharmacology & Therapeutics (2013) 93.
Heile, M., et al., "Cardiovascular Outcomes with Once-Weekly GLP-1 RAs: Clinical and Economic Implications" J Manag Care Spec Pharm (Sep. 2018) 24(9-a):S42-S52.
Hendarto, H., et al. "GLP-1 analog liraglutide protects against oxidative stress and albuminuria in streptozotocin-induced diabetic rats via protein kinase A-mediated inhibition of renal NAD (P) H oxidases." *Metabolism* 61, No. 10 (2012): 1422-1434.
Hernandez, A.F., et al. "Albiglutide and cardiovascular outcomes in patients with type 2 diabetes and cardiovascular disease (Harmony Outcomes): a double-blind, randomised placebo-controlled Trial" Lancet (Oct. 2018) 392:1519-29.
Heuvelman, V.D., et al., "Cardiovascular effects of glucagon-like peptide 1 receptor agonists: from mechanistic studies in humans to clinical outcomes" Cardiovascular Research (2020) 116, pp. 916-930. doi:10.1093/cvr/cvz323. Epub, Dec. 2019.
Holman, R.R., et al., "Effects of Once-Weekly Exenatide on Cardiovascular Outcomes in Type 2 Diabetes" The New England Journal of Medicine (2017) 377:1228-39.
Hussein, H. et al., "Systematic Review or Meta-analysis: Cardiovascular efficacy and safety of sodium-glucose co-transporter-2 inhibitors and glucagon-like peptide-1 receptor agonists: a systematic review and network meta-analysis" Diabetic Medicine (2019) 36(4) 444-452. Epub. Jan. 2019.
Weinstock R.S, et al., "Safety and efficacy of once-weekly dulaglutide versus sitagliptin after 2 years in metformin-treated patients with type 2 diabetes (AWARD-5): a randomized, phase III study" Diabetes Obes Metab. (2015) 17(9): 849-858.
Jendle J., et al., "Insulin and GLP-1 analog combinations in type 2 diabetes mellitus: a critical review" Expert Opin Investig Drugs. (2012) 21(10):1463-74. doi: 10.1517/13543784.2012.707190. Epub Jul. 16, 2012. PMID: 22799463.
Jendle J., et al., "Efficacy and safety of dulaglutide in the treatment of type 2 diabetes: a comprehensive review of the dulaglutide clinical data focusing on the AWARD phase 3 clinical trial program" Diabetes Metab Res Rev. (2016) 32(8):776-790.
Jendle J., et al., "Continuous glucose monitoring in patients with type 2 diabetes treated with glucagon-like peptide-1 receptor agonist dulaglutide in combination with prandial insulin lispro: an AWARD-4 substudy" Diabetes, Obesity and Metabolism (2016) 18(10) pp. 999-1005.
Kalra, S. "Follow the LEADER—liraglutide effect and action in diabetes: evaluation of cardiovascular outcome results trial." *Diabetes Therapy* (2016) vol. 7, No. 4, pp. 601-609.
Zhang, X., et al., "Cardiovascular and microvascular outcomes of glucagon-like peptide-1 receptor agonists in type 2 diabetes: a meta-analysis of randomized controlled cardiovascular outcome trials with trial sequential analysis" BMC Pharmacology and Toxicology (Sep. 2018) 19:58.
Liu, Q., et al. "The exenatide analogue AC3174 attenuates hypertension, insulin resistance, and renal dysfunction in Dahl salt-sensitive rats." *Cardiovascular diabetology* 9, No. 1 (2010): 32.
Loghin, C., et al., "LY2189265, a long-acting GLP-1 analog, does not prolong QTc interval in healthy subjects at supratherapeutic doses" Diabetes (2011) vol. 60, pp. A299-A299.
Lorenz M., et al., Differential effects of glucagon-like peptide-1 receptor agonists on heart rate. Cardiovasc Diabetol. (2017)16(1):6.
Mafham, M., et al., "HARMONY or discord in cardiovascular outcome trials of GLP-1 receptor agonists?" The Lancet (Published Online 2018) 392(10157) http://dx.doi.org/10.1016/S0140-6736(18)32348-1.

(56) References Cited

OTHER PUBLICATIONS

Mann JF, et al., "Liraglutide and Renal Outcomes in Type 2 Diabetes: Results of the LEADER Trial" Abstract HI-OR01, J. Am. Soc. Nephrol. 27 (2016).
Mann, J. Fe, et al. "Liraglutide and renal outcomes in type 2 diabetes." N. Engl. J. Med. 377, No. 9 (2017): 839-848.
Mari A., et al. "Differential effects of once-weekly glucagon-like peptide-1 receptor agonist dulaglutide and metformin on pancreatic β-cell and insulin sensitivity during a standardized test meal in patients with type 2 diabetes" Diabetes Obes Metab. (2016) 18(8):834-839.
Marso, S. P., et al. "Liraglutide and cardiovascular outcomes in type 2 diabetes." N. Engl. J. Med. 375, No. 4 (2016): 311-322. DOI: 10.1056/NEJMoa1603827.
Marso, S. P., et al. "Semaglutide and cardiovascular outcomes in patients with type 2 diabetes." N. Engl. J. Med. 375 (2016): 1834-1844.
Marso S.P., et al. "Supplement to: Semaglutide and cardiovascular outcomes in patients with type 2 diabetes" N. Engl. J. Med.; 375 (2016):1834-44. DOI: 10.1056/NEJMoa1607141.
Matfin, G., et al., "Safe and effective use of the once weekly dulaglutide single-dose pen in injection-naïve patients with type 2 Diabetes" Journal of diabetes science and technology (2015) 9(5) pp. 1071-1079.
Matza, L. S., et al., "Physician perceptions of GLP-1 receptor agonists in the UK" Current Medical Research and Opinion (2016) 32(5), pp. 857-864.
Milicevic, Z., et al., "Low incidence of anti-drug antibodies in patients with type 2 diabetes treated with once-weekly glucagon-like peptide-1 receptor agonist dulaglutide" Diabetes, Obesity and Metabolism (2016) 18(5), pp. 533-536.
Nauck M., et al., "Efficacy and safety of dulaglutide versus sitagliptin after 52 weeks in type 2 diabetes in a randomized controlled trial (AWARD-5)" Diabetes Care. (2014)37(8):2149-2158.
Nauck M., et al., "Assessment of pancreas safety in the development program of once-weekly GLP-1 receptor agonist dulaglutide" Diabetes Care. (2017)40(5):647-654.
Noriega, J., et al., "The Impact of LY2189265 (GLP-1 Analog) on Glycemic Control in Hispanic and Nonhispanic Caucasians With Uncontrolled Type 2 Diabetes: An Ego Study Analysis" Journal of Investigative Medicine (2010) vol. 58, No. 4, pp. 644-644. 530.
Novo Nordisk "Novo Nordisk's (NVO) CEO Lars Fruergaard J0rgensen on Fiscal Q3 2017 Results—Earnings Call Transcript" Seeking Alpha (Nov. 1, 2017).
Pantalone, K.M., et al., "Cardiovascular outcomes trials with glucagon-like peptide-1 receptor agonists: A comparison of study designs, populations and results" Diabetes, Obesity and Metabolism (Aug. 2020) vol. 22, Issue 12, pp. 2209-2226.
Park, C. W., et al. "Long-term treatment of glucagon-like peptide-1 analog exendin-4 ameliorates diabetic nephropathy through improving metabolic anomalies in db/db mice." *Journal of the American Society of Nephrology* 18, No. 4 (2007): 1227-1238.
Pechtner, V., et al. "A new approach to drug therapy: Fc-fusion technology" Prim Health Care (2017) 7(1).
Pfeffer, M.A., et al., "Lixisenatide in Patients with Type 2 Diabetes and Acute Coronary Syndrome" The New England Journal of Medicine (2015) 373:23, pp. 2247-2257.
Pozzilli, P., et al., "Placebo-controlled, randomized trial of the addition of once-weekly glucagon-like peptide-1 receptor agonist dulaglutide to titrated daily insulin glargine in patients with type 2 diabetes (AWARD-9)" Diabetes, Obesity and Metabolism (2017) 19(7) pp. 1024-1031.
Ratner, Robert E., MD "After 10 Years and 26 CVOTs, Where do We Stand on CV Safety in Diabetes?" Georgetown University School of Medicine, Washington DC, available at https://www.fda.gov/media/121275/download (Oct. 2018).
Reaney, M., et al., Treatment satisfaction in people with type 2 diabetes mellitus treated with once-weekly dulaglutide: data from the AWARD-1 and AWARD-3 clinical trials. Diabetes, Obesity and Metabolism (2015) 17(9) pp. 896-903.

Schernthaner, G., et al. "GLP-1 receptor agonists and cardiovascular risk in routine clinical practice" The Lancet, Diabetes & Endocrinology (2019) vol. 7, Issue 2, p. 78-80 Published Online Dec. 5, 2018 http://dx.doi.org/10.1016/S2213-8587(18)30340-1.
Sherman, S. I., et al., "No calcitonin change in a person taking dulaglutide diagnosed with pre-existing medullary thyroid cancer" Diabetic Medicine (Mar. 2018) 35(3) pp. 381-385.
Skrivanek Z., et al., "Application of adaptive design methodology in development of a long-acting glucagon-like peptide-1 analog (dulaglutide): statistical design and simulations" Journal of Diabetes Science and Technology (2012) vol. 6, Issue 6, pp. 1305-1318.
Skrivanek Z., et al., "Dose-finding results in an adaptive trial of dulaglutide combined withmetformin in type 2 diabetes (AWARD-5)" American Diabetes Association 73rd Meeting (2013).
Skrivanek Z., et al., "Dose-finding results in an adaptive, seamless, randomized trial of onceweekly dulaglutide combined with metformin in type 2 diabetes patients (AWARD-5)" Diabetes Obes Metab. (2014)16(8):748-756.
Stark Casagrande et al. The prevalence of meeting A1c, blood pressure, and LDL goals among people with diabetes, 1988-2010 Diabetes Care (2013) 36(8):2271-2279.
Sorensen, C. M., et al. "Renoprotective effects of dulaglutide in patients with T2DM and CKD." Nature Reviews Nephrology 14, No. 11 (Nov. 2018): 659-660.
Tanaka, A., et al., "Clinical application of glucagon-like peptide-1 receptor agonists in cardiovascular disease: lessons from recent clinical cardiovascular outcomes trials" Cardiovasc Diabetol (Jun. 2018) 17:85, 1-6.
Taylor "GLP-1 receptor agonists: differentiation within the class" Lancet Diabetes & Endocrinology (2018) vol. 6, Issue 2, p. 83-85, published online Dec. 2017.
Terauchi, Y., et al., "Monotherapy with the once weekly GLP-1 receptor agonist dulaglutide for 12 weeks in Japanese patients with type 2 diabetes: dose-dependent effects on glycaemic control in a randomised, double-blind, placebo-controlled study" Endocrine Journal (2014) EJ14-0147.
Tong, L., et al., (Apr. 2018). "Glycemic control of type 2 diabetes mellitus across stages of renal impairment: information for primary care providers" *Postgraduate medicine*, 130(4), 381-393.
Trulicity (dulaglutide) injection, for subcutaneous use, label, Reference ID: 4133133 (Aug. 2017).
Trulicity [Prescribing Information], Indianapolis, IN: Eli Lilly and Company, 2017. Available at: http://pi.lilly.com/us/trulicity-uspi.pdf . Accessed Oct. 18, 2017.
Trulicity [summary of product characteristics (SmPC)]. Houten, The Netherlands; 2017. Available at: http://www.ema_europa_eu/docs/en_GB/document_library/EPAR_Product_Information/human/002825/WC500179470.pdf Accessed Nov. 8, 2017.
Tuttle, K. R., et al., (2017). "Effects of once-weekly dulaglutide on kidney function in patients with type 2 diabetes in phase II and III clinical trials" *Diabetes, Obesity and Metabolism*, 19(3), 436-441.
Tuttle, K. R., et al., (Aug. 2018) "Dulaglutide versus insulin glargine in patients with type 2 diabetes and moderate-to-severe chronic kidney disease (AWARD-7): a multicentre, open-label, randomised trial" *The Lancet Diabetes & Endocrinology*, 6(8), 605-617.
Tuttle, K. R., et al., "Body weight and eGFR during dulaglutide treatment in type 2 diabetes and moderate-to-severe chronic kidney disease (AWARD-7)." *Diabetes, Obesity and Metabolism* 21, No. 6 (Feb. 2019): 1493-1497.
Tuttle, K. L. M., et al. "Comparable glycemic control, greater weight loss, and lower hypoglycemia with once weekly dulaglutide versus insulin glargine, both combined with Lispro, in type 2 diabetes and moderate to severe chronic kidney disease (AWARD-7)." Poster presented at: American Diabetes Association 74th Scientific Sessions (2017).
Tuttle, K. R., et al., "Dulaglutide vs. glargine, both combined with lispro, mitigated eGFR decline in people with type 2 diabetes and moderate-to-severe chronic kidney disease (AWARD-7)." In Diabetes, vol. 66, pp. LB37-LB38. (2017).

(56) References Cited

OTHER PUBLICATIONS

Tuttle, K.R., et al., "Lesser eGFR Decline with Dulaglutide Regardless of Weight Changes in People with Type 2 Diabetes and Moderate to Severe Chronic Kidney Disease (AWARD-7)" EASD (Oct. 2018).

Umpierrez G., et al., "The effects of LY2189265, a long-acting glucagon-like peptide-1 analogue, in a randomized, placebo-controlled, double-blind study of overweight/obese patients with type 2 diabetes: the EGO study" Diabetes, Obesity and Metabolism (2011) 13(5) pp. 418-425.

Umpierrez G., et al., Efficacy and safety of dulaglutide monotherapy versus metformin in type 2 diabetes in a randomized controlled trial (AWARD-3). Diabetes Care. (2014) 37(8):2168-2176.

Umpierrez G., et al., Relationship between weight change and glycaemic control in patients with type 2 diabetes receiving once-weekly dulaglutide treatment. Diabetes, Obesity and Metabolism (2016) 18(6) pp. 615-622.

Usborne, A., et al., "An investigative study of pancreatic exocrine biomarkers, histology, and histomorphometry in male Zucker diabetic fatty (ZDF) rats given dulaglutide by subcutaneous injection twice weekly for 13 weeks" Toxicologic pathology (2015) 43(8) pp. 1093-1102.

"Researching Cardiovascular Events With a Weekly Incretin in Diabetes (REWIND) (REWIND)" ClinicalTrials.gov (2011) NCT No. NCT01394952.

Wysham C., et al., "Efficacy and safety of dulaglutide added onto pioglitazone and metformin versus exenatide in type 2 diabetes in a randomized controlled trial (AWARD-1)" Diabetes Care. (2014) 37(8):2159-2167.

Vahle, J. L., et al., "Effects of the GLP-1 receptor agonist dulaglutide on the structure of the exocrine pancreas of cynomolgus monkeys" Toxicologic pathology (2015) 43(7), 1004-1014.

Vahle, J. L., et al., "Effects of dulaglutide on thyroid C cells and serum calcitonin in male Monkeys" Endocrinology (2015) 156(7) pp. 2409-2416.

Victoza (liraglutide) injection, for subcutaneous use, label Reference ID: 4144309 (Aug. 2017).

Eli Lilly and Company Lilly and Company, "Researching cardiovascular Events with a Weekly Incretin in Diabetes (REWIND)", ClinicalTrials.gov, NCT01394952, First Posted Jul. 15, 2011.

Office Action dated Jul. 23, 2021 in Canadian application No. 3,056,663.

Nov. 23, 2021 Response to Office Action dated Jul. 23, 2021 in Canadian application No. 3,056,663.

Claim Amendments—Clean Version, submitted with Nov. 23, 2021 Response to Office Action dated Jul. 23, 2021 in Canadian application No. 3,056,663.

Claim Amendments—Marked Version, Nov. 23, 2021 Response to Office Action dated Jul. 23, 2021 in Canadian application No. 3,056,663.

A Study Comparing Dulaglutide With Insulin Glargine on Glycemic Control in Participants With Type 2 Diabetes (T2D) and Moderate or Severe Chronic Kidney Disease (CKD) (AWARD-7), XP055497221, https://clinicaltrials.gov/ct2/show/NC_101621178, Last Update Posted Apr. 25, 2018.

Adler, et al., and UKPDS Group. "Development and progression of nephropathy in type 2 diabetes: the United Kingdom Prospective Diabetes Study (UKPDS 64)." *Kidney international* 63, No. 1 (2003): 225-232.

Alatorre, C., et al., "Treatment patterns in patients with type 2 diabetes mellitus treated with glucagon-like peptide-1 receptor agonists: Higher adherence and persistence with dulaglutide compared with once-weekly exenatide and liraglutide" Diabetes, Obesity and Metabolism (2017) 19(7) pp. 953-961.

American Association of Clinical Endocrinologists "Diabetes Therapy Highlights" May 16-20, 2018; Boston, MA; Day #3 Highlights; www.closeconcerns.com.

American Diabetes Association "Diabetes Care" The Journal of Clinical and Applied Research and Education (Jan. 2018) vol. 41, Supplement 1, ISSN 0149-5992.

American Diabetes Association "9. Pharmacologic Approaches to Glycemic Treatment: Standards of Medical Care in Diabetes—2019" Diabetes Care (Jan. 2019) vol. 42, Supplement 1, S90-S102.

American Diabetes Association "Executive Highlights—Full Coverage of Meeting Content diabetes therapy, technology, obesity/prediabetes, and big picture topics" ADA's 79th Scientific Sessions (Jun. 7-11, 2019) www.closeconcerns.com; ADA 2019 Full Report | Close Concerns Knowledgebase.

Bahtiyar, G., et al., "Cardiovascular Effects of Different GLP-1 Receptor Agonists in Patients with Type 2 Diabetes" Curr Diab Rep 18, 92 (Aug. 2018). https://doi.org/10.1007/s11892-018-1043-z.

Bain SC, et al. "Cardiovascular safety of oral semaglutide in patients with type 2 diabetes: Rationale, design and patient baseline characteristics for the PIONEER 6 trial" Diabetes Obes Metab. (Sep. 2019) 21(3) 499-508.

Barrington P., et al., "A 5-week study of the pharmacokinetics and pharmacodynamics of LY2189265, a novel, long acting glucagon-like peptide-1 analogue, in patients with type 2 diabetes." Diabetes Obes Metab. (2011) 13(5):426-433.

Barrington P., et al., "LY2189265, a long acting glucagon-like peptide-1 analogue, showed a dose-dependent effect on insulin secretion in healthy subjects" Diabetes Obes Metab. (2011)13(5):434-438.

Von Scholten, et al., "Renal Effects of Liraglutide in Type 2 Diabetic Patients with Albuminuria: A Randomized Clinical Trial" Abstract FR-PO815, J. Am. Soc. Nephrol. 27 (2016).

Bauduceau, B., "Update on a drug: dulaglutide (Trulicity©)" Médecine des maladies Métaboliques [Medicine of metabolic diseases] French Language (Feb. 2019) vol. 13, No. 1, p. 55-68.

Bethel, M.A., "Cardiovascular outcomes with glucagon-like peptide-1 receptor agonists in patients with type 2 diabetes: a meta-analysis" Lancet Diabetes Endocrinol (2017) vol. 6, Issue 2, p. 105-113.

Bibeau, W. S., et al., "Impact of out-of-pocket pharmacy costs on branded medication adherence among patients with type 2 diabetes" Journal of managed care & specialty pharmacy (2016) 22(11) pp. 1338-1347.

Blonde L., et al., "Once-weekly dulaglutide versus bedtime insulin glargine, both in combination with prandial insulin lispro, in patients with type 2 diabetes (AWARD-4): a randomised, open-label, phase 3, noninferiority study" Lancet (2015) 385(9982):2057-2066.

Botros, F. T. "Comparable glycaemic control with once weekly dulaglutide versus insulin glargine, both combined with lispro, in type 2 diabetes and chronic kidney disease (AWARD-7)" *Diabetologia* (Sep. 2017) vol. 60, pp. S3-S3. 233 Spring St, New York, NY 10013 USA: Springer.

Boustani, M. A., et al., "Similar efficacy and safety of once-weekly dulaglutide in patients with type 2 diabetes aged≥ 65 and< 65 years" Diabetes, Obesity and Metabolism (2016) 18(8) pp. 820-828.

Boye, K. S., et al., "Associations between adherence and outcomes among older, type 2 diabetes patients: evidence from a Medicare Supplemental database" Patient preference and adherence (2016) 10, 1573.

Boye, et al., "Glucagon-like peptide-1 receptor agonist use and renal impairment: a retrospective analysis of an electronic health records database in the US population." *Diabetes Therapy* 9, No. 2 (Feb. 2018): 637-650.

Boyle, et al., "Cardiovascular benefits of GLP-1 agonist in type 2 diabetes: A comparative review" Clinical Science (Aug. 2018) 132, pp. 1699-1709.

Byrd, R. A., et al., "Chronic toxicity and carcinogenicity studies of the long-acting GLP-1 receptor agonist dulaglutide in rodents" Endocrinology (2015) 156(7), 2417-2428.

Cherney, et al. "Dulaglutide and renal protection in type 2 diabetes." *The Lancet Diabetes & Endocrinology* (Jun. 2018) vol. 6, No. 8, 588-590.

Chien, J. Y., et al., "LY2189265, a Long-Acting Glucagon-Like Peptide 1 (GLP-1) Analog, Does Not Affect Gastric Emptying of Acetaminophen after Multiple Dosing in Healthy Subjects" Diabetes (Jun. 2010) vol. 59, pp. A164-A164.

Wysham C., et al., "Baseline factors associated with glycaemic response to treatment with once-weekly dulaglutide in patients with type 2 diabetes" Diabetes, Obesity and Metabolism (2016) 18(11) pp. 1138-1142.

(56) References Cited

OTHER PUBLICATIONS

Yu, M., et al., "Patient-reported outcomes in patients with type 2 diabetes treated with dulaglutide added to titrated insulin glargine (AWARD-9)" Clinical Therapeutics (2017) 39(11), 2284-2295.

Closer Look "Memorandum—Lilly 2Q17—Diabetes portfolio grows 30% YOY to $1.9B; Trulicity drives 61% portfolio growth with sales >doubling YOY to $480M; Jardiance sales surpass $100M; Humalog revenue declines 3% YOY to $678M" Jul. 26, 2017, www.closeconcerns.com.

Closer Look "Memorandum—Novo Nordisk 3Q17—Diabetes/obesity portfolio flat at $3.5 B (+5% YOY in local currencies); Tresiba up 66% YOY, EMA approves hypo benefit on label; Modern insulins fall 10% YOY; Strength in GLP-1; Future growth prospects in Fiasp, semaglutide" Nov. 2, 2017, www.closeconcerns.com.

Closer Look "Memorandum—Lilly releases topline REWIND results: Trulicity achieves superiority to placebo on three-point MACE in majority primary prevention population" Nov. 5, 2018, www.closeconcerns.com.

Closer Look "Memorandum—Lilly 2019 Financial Guidance + Investor Meeting—GIP /GLP-1 Tirzepatide to Enter Phase 3 for Obesity, Phase 2 for NASH; Rewind Submission in 1H19, Connected Pen+ Jardiance for Type 1 (?) in 2019; Early-Stage Basal Insulin Movement; R&D Strategy Overhaul" Dec. 19, 2018, www.closeconcerns.com.

Closer Look "Memorandum—Lilly 2019 Financial Guidance + Investor Meeting—GIP /GLP-1 Tirzepatide to Enter Phase 3 for Obesity, Phase 2 for NASH; Rewind Submission in 1H19, Connected Pen+ Jardiance for Type 1 (?) in 2019; Early-Stage Basal Insulin Movement; R&D Strategy Overhaul" Dec. 19, 2018, downloaded Jul. 19, 2021, www.closeconcerns.com.

Closer Look "Memorandum—Lilly 4Q18—Diabetes grows 25% in 2018 for $9.7 billion in revenue; Growth from Trulicity (+58% YOY to $3.2B), Basaglar (+85% to $801M), and Jardiance (+47% YOY to $658M); GDF15 agonist added to phase 1" Feb. 6, 2019, www.closeconcerns.com.

Closer Look "Memorandum—Lilly 1Q19—Diabetes +10% YOY, −5% sequentially to $2.5B; Trulicity +30% YOY to $880M, with 59% share of growth; Jardiance +35% YOY to ~$618M (16% SOG); Basaglar +51% YOY to $251M (25% SOG); Pipeline: FDA delays nasal glucagon decision, Jardiance for type 1 sNDA "refused to file" by FDA" Apr. 30, 2019, www.closeconcerns.com.

Closer Look "Memorandum—Novo Nordisk 1Q19—D/O sales +9% YOY (+5% CER), flat sequentially at $3.7B; Ozempic +44% seq. to $214M; Strong growth from Tresiba, Saxenda; GLP-1 value share leadership at 46.1%; Three semaglutide trials in CVD, CKD, and retinopathy starting in 2019" May 3, 2019, www.closeconcerns.com.

Zoungas, S., et al., "Effects of intensive glucose control on microvascular outcomes in patients with type 2 diabetes: a meta-analysis of individual participant data from randomised controlled trials." *The lancet Diabetes & endocrinology* 5, No. 6 (2017): 431-437.

Zweck, E. et al., "GLP-1 receptor agonists and cardiovascular disease: drug-specific or class effects?" The Lancet Diabetes & Endocrinology (Feb. 2019) vol. 7, Issue 2, p. 89-90.

Dalsgaard N.B., et al., "Effects of glucagon-like peptide-1 receptor agonists on cardiovascular risk factors: A narrative review of head-to-head comparisons" Diabetes Obes. Metab (Mar. 2018) 20:508-519.

Davidson, J. A., et al., "Efficacy and safety of dulaglutide in Hispanic/Latino patients with type 2 diabetes in the AWARD clinical program" Endocrine Practice (2016) 22(12) pp. 1406-1414.

Davies, M., et al., (2016). The treatment of type 2 diabetes in the presence of renal impairment: what we should know about newer therapies. *Clinical pharmacology: advances and applications*, 8, 61.

\* cited by examiner

SEQUENCE LISTING

<160> NUMBER OF SEQ ID NOS: 1

<210> SEQ ID NO 1
<211> LENGTH: 275
<212> TYPE: PRT
<213> ORGANISM: Artificial Sequence
<220> FEATURE:
<223> OTHER INFORMATION: Synthetic Construct

<400> SEQUENCE: 1

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Ser Gly Gly Gly Ser Ala Glu
        35                  40                  45

Ser Lys Tyr Gly Pro Pro Cys Pro Pro Cys Pro Ala Pro Glu Ala Ala
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
            85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
            165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
            245                 250                 255

Met His Glu Ala Leu His Asn His Tyr Thr Gln Lys Ser Leu Ser Leu
            260                 265                 270

Ser Leu Gly
    275
```

THERAPEUTIC USES OF DULAGLUTIDE

The present invention relates to the field of medicine. More particularly, the present invention relates to methods for reducing the risk of major adverse cardiovascular events in type 2 diabetes mellitus (T2DM) patients with multiple cardiovascular risk factors or established cardiovascular disease comprising administering the glucagon like peptide-1 (GLP-1) receptor agonist dulaglutide.

Patients with T2DM frequently suffer from a variety of comorbidities, one of which is cardiovascular disease (CVD). The incidence of CVD in T2DM patients is approximately twice than that in non-diabetic individuals, and modification of CVD risk factors, including diet and exercise, is a standard component of T2DM treatment plans, but CVD-related death remains the most common cause of death in T2DM patients.

The effects of both glucose lowering and non-glucose lowering therapies on the incidence of cardiovascular events have been studied. Studies have shown non-glucose lowering therapies, including statins, such as atorvastatin, renin angiotensin system modulators, such as ramipril and telmisartan, and combinations of perindopril, an angiotensin converting enzyme (ACE) inhibitor and indapamide, a thiazide diuretic (TZD), are capable of reducing the incidence of cardiovascular events in T2DM patients.

Studies on the effects of glucose-lowering therapies on the incidence of cardiovascular events have generated varying results. For example, pioglitazone had a mixed effect on cardiovascular outcomes, basal insulin and dipeptidyl peptidase-4 (DPP-4) inhibitors had a neutral effect on cardiovascular outcomes, and empagliflozin, a sodium-glucose co-transporter-2 (SGLT2) inhibitor, reduced cardiovascular mortality and hospitalization for heart failure.

Similarly, studies on the effects of different agents within the class of GLP-1 receptor agonists on the incidence of cardiovascular events have also generated varying results. On the one hand, lixisenatide was found to not significantly alter the rate of major adverse cardiovascular events or other serious adverse events in patients with established CVD (Pfeffer M A, et al. *Lixisenatide inpatients with type 2 diabetes and acute coronary syndrome*, 373 N. ENGL. J MED. 2247-2257 (2015) ("ELIXA")), and once weekly exenatide was found to not result in a significant difference in the incidence of major adverse cardiovascular events compared to placebo in a patient population including patients with and without established CVD (Holman R R, et al., *Effects of Once-Weekly Exenatide on Cardiovascular Outcomes in Type 2 Diabetes*, 377 N. ENGL. J. MED. 1228-1239 (2017) ("EXCSEL")). On the other hand, albiglutide, liraglutide and semaglutide were found to reduce the risk of major adverse cardiovascular events in patient populations comprised entirely (albiglutide) or predominantly (liraglutide and semaglutide) of patients with established CVD. (Hernandez A F, et al., *Albiglutide and Cardiovascular Outcomes in Patients with Type 2 Diabetes and Cardiovascular Disease (Harmony Outcomes): a Double-blind, Randomized Placebo-controlled Trial*, 392 LANCET 1519-1529 (2018) ("Harmony Outcomes"); Marso S P, et al., *Liraglutide and Cardiovascular Outcomes in Patients with Type 2 Diabetes*, 375 N. ENGL. J. MED. 311-322 (2016) ("LEADER")); Marso S P, et al., *Semaglutide and Cardiovascular Outcomes in Patients with Type 2 Diabetes* 375 N. ENGL. J. MED. 1834-1844 (2016) ("SUSTAIN-6")).

Despite the therapies described above, the need for new treatment options capable of reducing the risk of major adverse cardiovascular events in T2DM patients remains. In particular, the need remains for treatment options capable of reducing the risk of major adverse cardiovascular events in T2DM patients who do not already have established cardiovascular disease.

The methods of the present invention seek to meet those needs. Indeed, dulaglutide was recently found to be capable of statistically significantly reducing the risk of major adverse cardiovascular events in a population that included patients both with and without established cardiovascular disease. Moreover, the overall reduction in risk seen was driven by and similar in both patients with and without established cardiovascular disease.

Accordingly, the present invention provides a method of reducing the risk of major adverse cardiovascular events in a patient with type 2 diabetes mellitus, comprising administering dulaglutide in a therapeutically effective amount to the patient once weekly, wherein the patient has type 2 diabetes mellitus and either: multiple cardiovascular risk factors without established cardiovascular disease; or established cardiovascular disease.

In another aspect, the present invention provides a method of reducing the risk of major adverse cardiovascular events in a patient with type 2 diabetes mellitus, comprising: identifying a patient having type 2 diabetes mellitus and either multiple cardiovascular risk factors without established cardiovascular disease or established cardiovascular disease; and administering dulaglutide in a therapeutically effective amount to the patient once weekly.

In another aspect, the present invention provides a method of delaying the occurrence of major adverse cardiovascular events in a patient with type 2 diabetes mellitus, comprising administering dulaglutide in a therapeutically effective amount to the patient once weekly, wherein the patient has type 2 diabetes mellitus and either: multiple cardiovascular risk factors without established cardiovascular disease; or established cardiovascular disease.

In another aspect, the present invention provides a method of improving glycemic control and reducing the risk of first occurrence of a major adverse cardiovascular event in a patient with type 2 diabetes mellitus, comprising administering dulaglutide in a therapeutically effective amount to the patient once weekly, wherein the patient has type 2 diabetes mellitus and either: multiple cardiovascular risk factors without established cardiovascular disease; or established cardiovascular disease.

In another aspect, the present invention provides dulaglutide for use in reducing the risk of major adverse cardiovascular events in a patient with type 2 diabetes mellitus and either: multiple cardiovascular risk factors without established cardiovascular disease; or established cardiovascular disease.

In another aspect, the present invention provides use of dulaglutide for the preparation of a medicament for reducing the risk of major adverse cardiovascular events in a patient with type 2 diabetes and either: multiple cardiovascular risk factors without established cardiovascular disease; or established cardiovascular disease.

Dulaglutide is a human GLP-1 receptor agonist which comprises a dimer of a GLP-1 analog fused at its C-terminus via a peptide linker to the N-terminus of an analog of an Fc portion of an immunoglobulin, and is identified by CAS registry number 923950-08-7, which provides the following chemical name: 7-37-Glucagon-like peptide I [8-glycine,22-glutamic acid,36-glycine] (synthetic human) fusion protein with peptide (synthetic 16-amino acid linker) fusion protein with immunoglobulin G4 (synthetic human Fc fragment), dimer. Each monomer of dulaglutide has the amino acid sequence set forth in SEQ ID NO:1:

```
                                            (SEQ ID NO: 1)
HGEGTFTSDVSSYLEEQAAKEFIAWLVKGGGGGGGSGGGGSGGGGSAESK

YGPPCPPCPAPEAAGGPSVFLFPPKPKDTLMISRTPEVTCVVVDVSQEDP

EVQFNWYVDGVEVHNAKTKPREEQFNSTYRVVSVLTVLHQDWLNGKEYKC

KVSNKGLPSSIEKTISKAKGQPREPQVYTLPPSQEEMTKNQVSLTCLVKG

FYPSDIAVEWESNGQPENNYKTTPPVLDSDGSFFLYSRLTVDKSRWQEGN

VFSCSVMHEALHNHYTQKSLSLSLG.
```

The two monomers are attached by disulfide bonds between the cysteine residues at positions 55 and 58 of SEQ ID NO:1 to form the dimer. Dulaglutide's structure, function, production and use in treating T2DM is described in more detail in U.S. Pat. No. 7,452,966 and U.S. Patent Application Publication No. US20100196405. When used herein, the term "dulaglutide" refers to any GLP-1 receptor agonist protein dimer of two monomers having the amino acid sequence of SEQ ID NO:1, including any protein that is the subject of a regulatory submission seeking approval of a GLP-1 receptor agonist product which relies in whole or part upon data submitted to a regulatory agency by Eli Lilly and Company relating to dulaglutide, regardless of whether the party seeking approval of said protein actually identifies the protein as dulaglutide or uses some other term. Dulaglutide agonizes the GLP-1 receptor resulting in stimulation of insulin synthesis and secretion, and has been shown to provide improved glycemic control in T2DM patients.

It has now been discovered that dulaglutide is capable of reducing the risk of major adverse cardiovascular events in patients having T2DM and with either established cardiovascular disease or without established cardiovascular disease with multiple cardiovascular risk factors.

As noted above, the effects of several other GLP-1 receptor agonists on cardiovascular outcomes (referred to as a cardiovascular outcome trial, or "CVOT") had been previously studied, and the results of those studies were mixed, with some demonstrating a benefit in patients having T2DM and some not demonstrating such a benefit. Summaries of the enrollment in and composite MACE 3 results from those studies are provided below in Table 1.

TABLE 1

GLP-1 receptor agonist CVOTs enrollment and MACE3 results.

| | Semaglutide (SUSTAIN-6) | Liraglutide (LEADER) | Lixisenatide (ELIXA) | Exenatide QW (EXSCEL) | Albiglutide QW (Harmony Outcomes) |
|---|---|---|---|---|---|
| # of Patients | 3297 | 9340 | 6068 | 14752 | 9463 |
| Age | 65 (mean) | 64 (mean) | 60 (mean) | 62 (median) | 64 (mean) |
| Prior CVD | 83%$^a$ | 81%$^b$ | 100%$^c$ | 73%$^d$ | 100%$^e$ |
| Statin Use | 73% | 72% | 93% | 74% | 84% |
| BMI | 33 (mean) | 33 (mean) | 30 (mean) | 32 (median) | 32 (mean) |
| HbA1c | 8.7% (mean) | 8.7% (mean) | 7.7% (mean) | 8.0% (median) | 8.7% (mean) |
| # of events | 254 | 1302 | 805 | 1744 | 766 |
| Median follow up | 2.1 years | 3.8 years | 2.1 years | 3.2 years | 1.6 years |
| MACE 3 Hazard Ratio (CI) | 0.74 (0.58-0.95) | 0.87 (0.78-0.97) | 1.02 (0.89-1.17) | 0.91 (0.83-1.00) | 0.78 (0.68-0.90) |

$^a$83.0% established cardiovascular disease including CKD 3+, and 58.8% had established cardiovascular disease without CKD; $^b$Cardiovascular disease, cerebrovascular disease, PVD, CRF, CHF; $^c$Acute coronary event within 180 days before screening; $^d$73% at least one prior cardiovascular event (70% CAD, 24% PAD, 22% cerebrovascular disease); $^e$Coronary artery disease, cerebrovascular disease or peripheral arterial disease.

As seen in Table 1, the results of three of the studies suggested the agents tested had a positive effect, while the results of two of the studies did not show a statistically significant difference from placebo.

Moreover, even in those studies demonstrating a benefit, the positive results were driven by patients with established cardiovascular disease. As also seen in Table 1, two of the studies included only patients having prior CVD. With respect to the studies that did include patients without established CVD, a comparison of results for patients with established CVD vs. those without established CVD (but with multiple risk factors) in the remaining studies is provided below in Table 2.

TABLE 2

"No Prior CVD" refers to patients without established CVD (but with multiple risk factors). "Prior CVD" refers to patients with established CVD.

| Agent | Liraglutide | | Semaglutide | | Exenatide QW | |
|---|---|---|---|---|---|---|
| Population | No Prior CVD (N = 1742; 18.7%) | Prior CVD (N = 7598; 81.3%) | No Prior CVD (N = 562; 17.0%) | Prior CVD (N = 2735; 83.0%) | No Prior CVD (N = 3970; 26.9%) | Prior CVD (N = 10782; 73.1%) |

TABLE 2-continued

"No Prior CVD" refers to patients without established CVD (but with multiple risk factors). "Prior CVD" refers to patients with established CVD.

| Agent | Liraglutide | | Semaglutide | | Exenatide QW | |
|---|---|---|---|---|---|---|
| MACE 3 Hazard ratio (CI) | 1.20 (0.86-1.67) | 0.83 (0.74-0.93) | 1.00 (0.41-2.46) | 0.72 (0.55-0.93) | 0.99 (0.77-1.28) | 0.90 (0.82-1.00) |
| | Interaction P = 0.04 | | Interaction P = 0.49 | | Interaction P = 0.50 | |

As seen above in Table 2, in none of the studies which enrolled patients without established CVD did that population of patients drive improvements in major adverse cardiovascular events. Contrarily, as described in more detail in the Examples below, treatment with dulaglutide was found to be capable of statistically significantly reducing the risk of major adverse cardiovascular events in a population that included patients with and without established cardiovascular disease, and that reduction in risk seen was driven by, and similar in, both of those groups of patients.

When used herein to characterize a patient, the term "established CVD" or "established cardiovascular disease" refers to a patient having one or more of the following: prior myocardial infarction (MI); prior ischemic stroke; prior unstable angina; prior revascularization (coronary, carotid or peripheral); prior hospitalization for ischemia-related events (unstable angina or myocardial ischemia on imaging or need for percutaneous coronary intervention); and prior documented myocardial ischemia.

When used herein, the term "major adverse cardiovascular events" refers to cardiovascular death, non-fatal myocardial infarction and non-fatal stroke. These events are also sometimes referred to as MACE or MACE 3 events. The first to occur of any of these events is a composite endpoint frequently used in CVOTs.

When used herein in relation to major adverse cardiovascular events, the term "risk factors" refers to characteristics of T2DM patients understood to increase their risk for a major adverse cardiovascular event. Such risk factors include in particular any of the following: current tobacco use (any form of tobacco); use of at least 1 approved lipid modifying therapy (e.g., statins such as atorvastatin, rosuvastatin, simvastatin, pravastatin, lovastatin, fluvastatin or pitavastatin; PCSK9 inhibitors, such as evolocumab or alirocumab; and ezetimibe) to treat hypercholesterolemia or a documented untreated low-density lipoprotein cholesterol (LDL-C) ≥3.4 mmol/L (130 mg/dL) within the past 6 months; documented treated or untreated high-density lipoprotein cholesterol (HDL-C) <1.0 mmol/L (40 mg/dL) for men and <1.3 mmol/L (50 mg/dL) for women or triglycerides ≥2.3 mmol/L (200 mg/dL) within the past 6 months; use of at least 1 blood pressure medication to treat hypertension (e.g., angiotensin converting enzyme (ACE) inhibitors, angiotensin receptor blockers (ARBs), thiazidelike diuretics, and dihydropyridine calcium channel blockers) or untreated systolic blood pressure (SBP) ≥140 mm Hg or diastolic blood pressure (DBP) ≥95 mmHg; measured waist-to-hip ratio >1.0 for men and >0.8 for women.

When used herein, the term "multiple" means more than one.

When used herein, the terms "treatment," "treat," "treating," and the like, are meant to include slowing or attenuating the progression of a disease or disorder. These terms also include alleviating, ameliorating, attenuating, eliminating, or reducing one or more symptoms of a disorder or condition, even if the disorder or condition is not actually eliminated and even if progression of the disorder or condition is not itself slowed or reversed.

When used herein in connection with the risk of a major adverse cardiovascular event, the terms "reduce," "reduced," "reduces," "reducing," and the like, refer to a reduction in the probability of the occurrence of a major adverse cardiovascular event. When used herein, the term "delaying the occurrence" of a major adverse cardiovascular event, means increasing the period of time until the occurrence of a major adverse cardiovascular event.

When used herein in connection with multiple outcomes, the term "composite" refers to the first to occur of any of the outcomes.

When used herein, the term "hazard ratio" refers to a measure of the relative rate of progression to an endpoint as compared to a control group. In outcome-based clinical trials, such as the CVOTs described herein, a reduction in the hazard ratio for a test arm as compared to the control indicates the therapy used in the test arm reduces the risk of the endpoint, in the case of the studies described herein, major adverse cardiovascular events.

The methods and uses described herein may be provided in simultaneous or sequential combination with a standard of care for reducing the risk of major adverse cardiovascular events, which includes administering the maximum tolerated dose of ACE inhibitors and ARBs, and adequate treatment of blood pressure, lipids, and HbA1c to the local guidelines. In certain embodiments, the methods described herein further comprise administering to the patient the maximum tolerated dose of an ACE inhibitor. In certain embodiments, the methods described herein further comprise administering to the patient the maximum tolerated dose of an ARB. Other agents which may be administered include beta blockers, calcium channel blockers, diuretics, antithrombotic agents, aspirin and statins.

"Therapeutically effective amount" means the amount of dulaglutide for the methods and uses of the present invention or pharmaceutical composition comprising dulaglutide for the methods and uses of the present invention that will elicit the biological or medical response of or desired therapeutic effect on the patient that is being sought by the researcher, medical doctor, or other clinician. An effective amount of dulaglutide may vary according to factors such as the disease state, age, sex, and weight of the individual, and the ability of dulaglutide to elicit a desired response in the individual. An effective amount is also one in which any toxic or detrimental effect is outweighed by the therapeutically beneficial effects. In certain embodiments, the therapeutically effective amount of dulaglutide for use in the methods described herein is selected from the group consisting of 1.5, 3.0 and 4.5 mg. In certain embodiments, the therapeutically effective amount of dulaglutide is 3.0 mg. In certain embodiments, the therapeutically effective amount of dulaglutide is 4.5 mg. In preferred embodiments, the therapeutically effective amount of dulaglutide is 1.5 mg.

Additional embodiments of the present invention are described below:

A method of reducing the risk of major adverse cardiovascular events in a patient with type 2 diabetes mellitus, comprising administering dulaglutide in a therapeutically effective amount to the patient once weekly, wherein the patient has type 2 diabetes mellitus and either: multiple cardiovascular risk factors without established cardiovascular disease; or established cardiovascular disease.

A method of reducing the risk of major adverse cardiovascular events in a patient with type 2 diabetes mellitus, comprising: identifying a patient having type 2 diabetes mellitus and either multiple cardiovascular risk factors without established cardiovascular disease or established cardiovascular disease; and administering dulaglutide in a therapeutically effective amount to the patient once weekly.

A method of delaying the occurrence of major adverse cardiovascular events in a patient with type 2 diabetes mellitus, comprising administering dulaglutide in a therapeutically effective amount to the patient once weekly, wherein the patient has type 2 diabetes mellitus and either: multiple cardiovascular risk factors without established cardiovascular disease; or established cardiovascular disease.

A method of improving glycemic control and reducing the risk of first occurrence of a major adverse cardiovascular event in a patient with type 2 diabetes mellitus, comprising administering dulaglutide in a therapeutically effective amount to the patient once weekly, wherein the patient has type 2 diabetes mellitus and either: multiple cardiovascular risk factors without established cardiovascular disease; or established cardiovascular disease.

A method of improving glycemic control in a patient with type 2 diabetes mellitus, comprising administering dulaglutide in a therapeutically effective amount to the patient once weekly, wherein the patient has type 2 diabetes mellitus and either: multiple cardiovascular risk factors without established cardiovascular disease; or established cardiovascular disease; and wherein the risk of a major adverse cardiovascular event in the patient is reduced.

In an embodiment, the risk of a major adverse cardiovascular event is reduced by at least about 10%.

In an embodiment, the risk of a major adverse cardiovascular event is reduced by at least about 11%.

In an embodiment, the risk of a major adverse cardiovascular event is reduced by about 12%.

In an embodiment, the risk of cardiovascular death is lower.

In an embodiment, the risk of non-fatal stroke is lower.

In an embodiment, the risk of non-fatal myocardial infarction is lower.

In an embodiment, the risk of the occurrence of a composite of the following outcomes is reduced: diabetic retinopathy needing laser, anti-VEGF therapy, or vitrectomy; clinical proteinuria; a 30% decline in eGFR; or chronic renal replacement therapy.

In an embodiment, the patient has multiple cardiovascular risk factors without established cardiovascular disease.

In an embodiment, the risk factors for cardiovascular disease are selected from the group consisting of: current tobacco use (any form of tobacco); use of at least 1 approved lipid modifying therapy to treat hypercholesterolemia or a documented untreated low-density lipoprotein cholesterol (LDL-C) 23.4 mmol/L (130 mg/dL) within the past 6 months; documented treated or untreated high-density lipoprotein cholesterol (HDL-C) <1.0 mmol/L (40 mg/dL) for men and <1.3 mmol/L (50 mg/dL) for women or triglycerides ≥2.3 mmol/L (200 mg/dL) within the past 6 months; use of at least 1 blood pressure medication to treat hypertension or untreated systolic blood pressure (SBP) ≥140 mm Hg or diastolic blood pressure (DBP) 295 mmHg; measured waist-to-hip ratio >1.0 for men and >0.8 for women.

In an embodiment, the amount of dulaglutide is selected from the group consisting of about 1.5 mg, about 3.0 mg and about 4.5 mg.

In an embodiment, the amount of dulaglutide is about 1.5 mg.

In an embodiment, the amount of dulaglutide is about 3.0 mg.

In an embodiment, the amount of dulaglutide is about 4.5 mg.

In an embodiment, once weekly administration of dulaglutide is continued for approximately 5 years.

In an embodiment, the patient is also administered the standard of care for reducing the risk of major adverse cardiovascular events.

In an embodiment, the patient is also administered the maximum tolerated dose of an ACE inhibitor.

In an embodiment, the patient is also administered the maximum tolerated dose of an ARB.

In an embodiment, the patient is also administered a beta blocker.

In an embodiment, the patient is also administered a calcium channel blocker.

In an embodiment, the patient is also administered a diuretic.

In an embodiment, the patient is also administered an antithrombotic agent.

In an embodiment, the patient is also administered aspirin.

In an embodiment, the patient is also administered a statin.

Dulaglutide for use in any of the above embodiments.

Use of dulaglutide in the preparation of a medicament for any of the above embodiments.

EXAMPLES

A phase 3 clinical study named Researching Cardiovascular Events with a Weekly INcretin in Diabetes (REWIND) is designed to assess the effect of once-weekly administration of dulaglutide compared to placebo on major adverse CV events when added to the existing antihyperglycemic regimen of patients with type 2 diabetes who are at high risk for CV events. The enrollment criteria, set forth in Table 3 below, are designed to include participants who are similar to patients seen within a typical diabetes practice, who have varying cardiovascular risk factors or established cardiovascular disease:

TABLE 3

| Enrollment Criteria. Key inclusion criteria |
| --- |
| T2DM with HbA1c ≤ 9.5% |
| Stable dose of 0, 1 or 2 oral glucose-lowering drugs ± basal insulin for ≥3 months |
| BMI ≥ 23 kg/m² |
| If age ≥50 years, at least 1 of: prior MI; prior ischaemic stroke; coronary revascularization ≥2 years earlier; carotid or peripheral revascularization ≥2 months earlier; unstable angina hospitalization; image proven myocardial ischaemia; or percutaneous coronary intervention |
| If age ≥55 years, any of the above or at least 1 of: documented myocardial ischaemia by stress test or imaging; |

TABLE 3-continued

Enrollment Criteria.
Key inclusion criteria

>50% coronary, carotid or lower extremity artery stenosis; ankle-brachial index <0.9; eGFR persistently <60 mL/min/1.73 m2; hypertension with left ventricular hypertrophy; or persistent albuminuria If age ≥60 years, any of the above or at least 2 of: any tobacco use; use of lipid-modifying therapy or a documented untreated LDL cholesterol ≥3.4 mmol/L (130 mg/dL) within the past 6 months; HDL cholesterol <1.0 mmol/L (40 mg/dL) for men and <1.3 mmol/L (50 mg/dL) for women or triglycerides ≥2.3 mmol/L (200 mg/dL) within the past 6 months; use of ≥1 blood pressure drug or untreated systolic blood pressure ≥140 mm Hg or diastolic blood pressure ≥95 mm Hg; or waist-to-hip ratio >1.0 (men) and >0.8 (women)

Run-in adherence to study drug = 100%

Signed informed consent

The study is designed to consist of a screening visit followed by a single-blind 3 week placebo run-in period. Afterwards, patients are randomized to either dulaglutide 1.5 mg or placebo and followed at approximately 6-month intervals. Patients are followed until approximately 1200 patients experience a primary endpoint event, adjudicated as such.

The primary efficacy measure is time to first occurrence (after randomization) of the composite endpoint of death from CV causes, nonfatal myocardial infarction (MI), or nonfatal stroke. Secondary outcomes include each component of the primary composite cardiovascular outcome, a composite clinical microvascular outcome comprising retinal or renal disease, hospitalization for unstable angina, heart failure requiring hospitalization or an urgent heart failure visit, and all-cause mortality. These outcomes are noted in Table 4. All deaths and cardiovascular, pancreatic and thyroid events (i.e. both efficacy and safety outcomes) are adjudicated by an external adjudication committee, which is blinded to treatment allocation.

TABLE 4

Secondary and safety outcomes.

| Secondary outcomes | Safety outcomes |
| --- | --- |
| Composite microvascular outcome: diabetic retinopathy needing laser, anti-VEGF therapy, or vitrectomy; or clinical proteinuria; or a 30% decline in eGFR; or chronic renal replacement therapy | Acute pancreatitis |
| Unstable angina hospitalization | Serious gastrointestinal events |
| Heart failure hospitalization or urgent visit | Cancers: pancreatic, medullary thyroid, other thyroid, other (excluding non-melanoma skin cancers) |
| Non-fatal MI | Severe hypoglycaemia |
| Non-fatal stroke | Immune reactions |

TABLE 4-continued

Secondary and safety outcomes.

| Secondary outcomes | Safety outcomes |
| --- | --- |
| Cardiovascular death | Serious hepatic events |
| Death | Serious renal events |
| | Supraventricular arrhythmias and cardiovascular conduction disorders |
| | Drug discontinuation |

Abbreviations: VEGF, vascular endothelial growth factor; eGFR, estimated glomerular filtration rate.

Sample size calculations are based on a 3-year recruitment period, an anticipated primary outcome event rate of 2% per year in the control group, annual dropout rate of 0.15%, and a 2-sided type I error of 5%. These assumptions indicate that recruitment of 9600 patients would result in a total of 1200 participants with at least 1 primary cardiovascular outcome over a maximum follow-up period of 8 years, and would provide 90% power to detect a hazard ratio of 0.82 for cardiovascular events. Follow-up ends after 1200 participants have had a primary cardiovascular outcome confirmed by adjudication.

All efficacy and safety analyses are designed to be conducted using an intention-to-treat approach that includes all randomized participants regardless of adherence. Baseline continuous variables are summarized as either means or medians with their standard deviations or interquartile ranges, and categorical variables are intended to be summarized as the number and percentage. The effect of the intervention on the time to the first occurrence of the primary outcome are designed to be analyzed using Cox proportional hazards models with the only independent variable being allocation to dulaglutide vs placebo. The proportional hazard assumptions are to be assessed graphically. Kaplan-Meier curves are to be generated along with log-rank P values. The incidence rates per 100 person years are to be calculated for each treatment group for all key outcomes. All secondary outcomes are to be analyzed in a predetermined order defined by a graphical approach to control the overall type I error. If the null hypothesis of no effect is rejected for the primary outcome, the graphical testing approach allocates the a parsimoniously for each secondary outcome. Exploratory subgroups to be examined include patients with prior CVD vs. those with no known CVD. For subgroup analyses, an interaction P value of <0.1 is considered suggestive of an interaction. No adjustments for multiplicity are to be performed.

12,137 individuals were screened, and 9901 individuals in 370 sites located in 24 countries were randomly allocated to either dulaglutide or placebo. The main reasons for not being randomized include not meeting eligibility criteria (68%) or personal decision (25%). The first participant was randomized in August 2011 and recruitment ended in August 2013. As noted in Tables 5 and 6, the mean age of participants was 66 years, the mean BMI was 32 kg/m$^2$ and 31% had a history of CVD (defined as a history of MI, ischaemic stroke, revascularization, hospitalization for unstable angina with concordant new ischaemic ECG changes, or a positive stress test with concordant imaging). In addition, 93% had a history of hypertension, 9% had a history of prior heart failure, and mean blood pressure was 137/78 mmHg. The mean reported duration of diabetes was 10 years, 24% of participants were taking insulin, 81% were taking metformin, 57% were on a sulphonylurea, and the mean baseline HbA1c was 7.3%. An angiotensin-converting enzyme (ACE) inhibitor or angiotensin receptor blocker (ARB) was used by 81% of participants, 45% were taking a β-blocker, 66% were taking a statin at baseline, 51% were on acetylsalicylic acid, 8% were on other antiplatelet agents, and the mean baseline LDL cholesterol was 2.56 nmol/L.

TABLE 5

Baseline clinical characteristics of 9901 randomized participants.

| Characteristic | All participants |
|---|---|
| Age, years: mean (s.d.) | 66.2 (6.5) |
| Females, n (%) | 4589 (46.3) |
| Geography, n (%) | |
| USA and Canada | 2071 (20.9) |
| Mexico and South America | 3021 (30.5) |
| Europe, Russia and South Africa | 4339 (43.8) |
| Asia: Taiwan and Korea | 148 (1.5) |
| Pacific: Australia and New Zealand | 322 (3.3) |
| Prior cardiovascular disease (≥1 of the following 6), n (%) | 3111 (31.4) |
| Prior MI | 1600 (16.2) |
| Prior ischemic stroke | 526 (5.3) |
| Prior unstable angina | 587 (5.9) |
| Prior revascularization[a] | 1787 (18.1) |
| Prior hospitalization for ischaemia-related events[b] | 1193 (12.1) |
| Prior documented myocardial ischaemia | 922 (9.3) |
| Prior hypertension, n (%) | 9223 (93.2) |
| Prior heart failure, n (%) | 852 (8.6) |
| Prior diabetic retinopathy, n (%) | 891 (9.0) |
| Prior fracture, n (%) | 1510 (15.3) |
| Prior cholecystectomy, n (%) | 1465 (14.8) |
| Current tobacco use, n (%) | 1407 (14.2) |
| Diabetes duration, years: mean (s.d.) | 10.0 (7.2) |
| Weight, kg: mean (s.d.) | 88.7 (18.5) |
| BMI, kg/m$^2$: mean (s.d.) | 32.3 (5.7) |
| Blood pressure, mm Hg: mean (s.d.) | 137.2 (16.8)/78.5 (9.8) |
| Pulse, beats/min: mean (s.d.) | 71.5 (10.9) |
| Male waist-to-hip ratio: mean (s.d.) | 110.6 (13.1)/108.4 (11.2) |
| Female waist-to-hip ratio: mean (s.d.) | 106.7 (13.1)/113.3 (13.7) |
| HbA1c, %: mean (s.d.) | 7.3 (1.1) |
| Cholesterol, mmol/L: mean (s.d.) | 4.52 (1.16) |
| LDL cholesterol, mmol/L: mean (s.d.) | 2.56 (0.98) |
| HDL cholesterol, mmol/L: mean (s.d.) | 1.18 (0.34) |
| Triglycerides, mmol/L: median (IQR) | 1.60 (1.17, 2.22) |
| eGFR, mL/min/1.73 m2: mean (s.d.) | 77.6 (24.1) |
| eGFR <60 mL/min/1.73 m$^2$, n (%) | 2199 (22.2) |
| Albumin/creatinine, mg/mmol: median (IQR) | 1.94 (0.75, 8.02) |
| Macro or microalbuminuria[c], n (%) | 3491 (35.3) |

Abbreviations: IQR, interquartile range; s.d., standard deviation; [a]Coronary, carotid or peripheral; [b]Unstable angina or myocardial ischaemia on imaging, or need for percutaneous coronary intervention; [c]Albumin/creatinine ≥3.39 mg/mmol.

TABLE 6

Baseline use of drug classes in randomized participants.

| Diabetes-specific drugs classes | | Other drug classes | |
|---|---|---|---|
| None | 600 (6.1) | ACE inhibitor | 4909 (49.6) |
| Only 1 oral agent | 4926 (49.8) | ARB | 3366 (34.0) |
| Only 2 oral agents | 3894 (39.3) | ACE inhibitor or ARB | 8054 (81.4) |
| Any insulin | 2398 (24.2) | Aldosterone antagonist | 464 (4.7) |
| Metformin | 8016 (81.0) | All diuretic | 4592 (46.4) |
| Glibenclamide/glyburide | 1271 (12.8) | Thiazides | 652 (6.6) |
| Other sulfonylureas | 4373 (44.2) | β blocker | 4502 (45.5) |
| DPP-4 inhibitors | 88 (0.9) | Ca channel blocker | 3385 (34.2) |
| SGLT2 inhibitors | 12 (0.1) | Acetylsalicylic acid | 5001 (50.5) |
| Meglitinides | 64 (0.7) | Other antiplatelet | 820 (8.3) |
| α-Glucosidase inhibitors | 118 (1.2) | Statin | 6537 (66.0) |
| Thiazolidinediones | 168 (1.7) | Fibrate | 892 (9.0) |
| Dopamine agonist | 47 (0.5) | Other lipid drug | 112 (1.1) |
| Other | 84 (0.9) | Proton pump inhibitor | 1673 (16.9) |

Values represent counts and percentage of all randomized.

Patients were and followed until August 2018. During a median follow-up of 5.4 years (interquartile range 5.1, 5.9) comprising 51,820 person-years, the final composite outcome status was known in 9610 patients. 1731 participants allocated to dulaglutide and 1761 participants allocated to placebo had at least 1 discontinuation of study drug during follow-up, while 4277 allocated to dulaglutide and 4196 allocated to placebo were taking study drug at the last visit. Participants allocated to dulaglutide or placebo respectively took study drug for 85.8% and 87.1% of the follow-up time from randomization until either they experienced the primary outcome or had a final follow-up.

Results are provided in Tables 7 and 8 below.

TABLE 7

Effect of dulaglutide on the primary and secondary outcomes.

| | Dulaglutide (N = 4949) | Placebo (N = 4952) | |
|---|---|---|---|
| Outcome | N (%) | N (%) | HR (95% CI) |
| MACE | 594 (12.0) | 663 (13.4) | 0.88 (0.79, 0.98) |
| MI | 223 (4.5) | 231 (4.7) | 0.96 (0.80, 1.15) |
| Stroke | 158 (3.2) | 205 (4.1) | 0.76 (0.62, 0.94) |
| CV Death | 317 (6.4) | 346 (7.0) | 0.91 (0.78, 1.06) |
| Composite microvascular | 1072 (21.7) | 1221 (24.7) | 0.85 (0.78, 0.92) |
| Unstable angina | 88 (1.8) | 77 (1.6) | 1.14 (0.84, 1.55) |
| Heart failure | 213 (4.3) | 226 (4.6) | 0.93 (0.77, 1.12) |
| All mortality | 536 (10.8) | 592 (12.0) | 0.90 (0.80, 1.01) |

As seen in Table 7, a weekly injection of dulaglutide significantly and safely reduced the hazard of CV outcomes by 12% compared to placebo. Moreover, the benefit was consistent across all 3 components of the composite primary outcome, with the largest estimated effect size being noted for nonfatal stroke. The incidence of the composite microvascular outcome was also lower in participants allocated to dulaglutide versus placebo.

TABLE 8

Subgroup analysis.

| Subgroup | Dulaglutide Events/Total (%) | Placebo Events/Total (%) | HR (95% CI) | P value for Interaction |
|---|---|---|---|---|
| Prior CVD | 280/1560 (17.9) | 315/1554 (20.3) | 0.87 (0.74-1.02) | 0.80 |
| No Known Prior CVD | 314/3389 (9.3) | 3487/3398 (10.2) | 0.89 (0.76-1.04) | |

As seen in table 8, the positive effect of dulaglutide on the primary outcome was similar in participants with and without a prior CV event.

We claim:

1. A method of reducing the risk of non-fatal stroke in a patient with type 2 diabetes mellitus comprising administering a therapeutically effective amount of dulaglutide to the patient once weekly, wherein the patient has type 2 diabetes mellitus and either: (a) multiple cardiovascular risk factor without established disease; or (b) established cardiovascular disease; and wherein the method reduces the risk of non-fatal stroke by at least about 10%.

2. The method of claim 1, wherein the cardiovascular risk factors are selected from the group consisting of (a), (b), (c), (d) and (e):
   (a) tobacco use;
   (b) at least 1 of:
       i) use of at least 1 approved lipid modifying therapy to treat hypercholesterolemia; or
       ii) a documented untreated low-density lipoprotein cholesterol (LDL-C) ≥3.4 mmol/L (130 mg/dL) within the past 6 months;

(c) at least 1 of:
  i) high-density lipoprotein cholesterol (HDL-C) measurement within the past 6 months of: <1.0 mmol/L (40 mg/dL) for men; and <1.3 mmol/L (50 mg/dL) for women; or
  ii) triglycerides ≥2.3 mmol/L (200 mg/dL) within the past 6 months;
d) at least 1 of:
  i) use of at least 1 blood pressure medication to treat hypertension; or
  ii) untreated systolic blood pressure (SBP) ≥140 mm Hg or diastolic blood pressure (DBP) ≥95 mmHg; and
(e) measured waist-to-hip ratio >1.0 for men and >0.8 for women.

3. The method of claim 1, wherein the therapeutically effective amount of dulaglutide is selected from the group consisting of 1.5 mg, 3.0 mg and 4.5 mg.

4. The method of claim 1, wherein the therapeutically effective amount of dulaglutide is 1.5 mg.

5. The method of claim 1, wherein the once weekly administration of dulaglutide is continued for approximately 5 years.

6. The method of claim 1, further comprising administering to the patient one or more of the following: an angiotensin converting enzyme (ACE) inhibitor; an angiotensin receptor blocker (ARB); a beta blocker; a calcium channel blocker; a diuretic; an antithrombotic agent; acetylsalicylic acid or a statin.

7. The method of claim 1, wherein the patient has multiple cardiovascular risk factors without established cardiovascular disease.

8. The method of claim 1, wherein the method reduces the risk of non-fatal stroke by at least about 20%.

* * * * *